(12) United States Patent
Shinya

(10) Patent No.: US 7,829,743 B2
(45) Date of Patent: Nov. 9, 2010

(54) SULFONIUM BORATE COMPLEX

(75) Inventor: Yoshihisa Shinya, Tochigi (JP)

(73) Assignees: Sony Corporation, Tokyo (JP); Sony Chemical & Information Device Corporation, Tokyo (JP)

( * ) Notice: Subject to any disclaimer, the term of this patent is extended or adjusted under 35 U.S.C. 154(b) by 0 days.

(21) Appl. No.: 12/311,657

(22) PCT Filed: Mar. 18, 2008

(86) PCT No.: PCT/JP2008/054922

§ 371 (c)(1),
(2), (4) Date: Apr. 8, 2009

(87) PCT Pub. No.: WO2008/149592

PCT Pub. Date: Dec. 11, 2008

(65) Prior Publication Data

US 2010/0022801 A1   Jan. 28, 2010

(30) Foreign Application Priority Data

Jun. 7, 2007   (JP)   ............... 2007-151203

(51) Int. Cl.
*C07F 5/02* (2006.01)
(52) U.S. Cl. ........................................................ 568/6
(58) Field of Classification Search ................ None
See application file for complete search history.

(56) References Cited

FOREIGN PATENT DOCUMENTS

| EP | 0 393 893 | * | 10/1990 |
|---|---|---|---|
| EP | 0 393 893 A1 | | 10/1990 |
| FR | 2727416 | * | 5/1996 |
| JP | A-3-205405 | | 9/1991 |
| JP | A-3-237107 | | 10/1991 |
| JP | A-4-1177 | | 1/1992 |
| JP | A-5-230189 | | 9/1993 |
| JP | A-9-176112 | | 7/1997 |
| JP | A-0-245378 | | 9/1998 |
| JP | A-10-310587 | | 11/1998 |

OTHER PUBLICATIONS

Toba et al., {"Cationic Photopolymerization of Epoxides by Direct and Sensitized Photolysis of Onium Tetrakis (pentafluorophenyl) borate Initiators," Macromolecule, 1999, pp. 3209-3215, vol. 32, No. 10}.*
International Preliminary Report on Patentability issued on Dec. 7, 2009 in corresponding International Application No. PCT/JP2008/054922 (with translation).
Toba, "Onium Borate o Mochiita Hikari Jugo Kaishizaikei no Kochiku," *Japanese Journal of Polymer Science and Technology*, 2002, pp. 449-459, vol. 59, No. 8.
Toba et al., "Cationic Photopolymerization of Epoxides by Direct and Sensitized Photolysis of Onium Tetrakis (pentafluorophenyl) borate Initiators," *Macromolecule*, 1999, pp. 3209-3215, vol. 32, No. 10.
Ikeda et al., "Effect of Counter Anions on the Lewis Acidity of Lithium Ion in Trityl Cation Formation," *The Reports of Institute of Advanced Material Study Kyoshu University*, 2001, pp. 169-175, vol. 15, No. 2.

* cited by examiner

*Primary Examiner*—Daniel M Sullivan
*Assistant Examiner*—Chukwuma O Nwaonicha
(74) *Attorney, Agent, or Firm*—Oliff & Berridge, PLC

(57) ABSTRACT

A novel sulfonium borate complex, which can reduce the amount of fluorine ions produced during thermal cationic polymerization, and realize low-temperature, rapid curing properties in a thermal cationic polymerizable adhesive, is represented by the structure of the following formula (1).

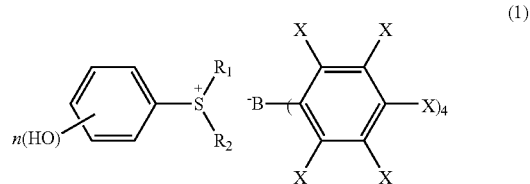

In the formula (1), $R_1$ is an aralkyl group and $R_2$ is a lower alkyl group. However, when $R_2$ is a methyl group, $R_1$ is not a benzyl group. X is a halogen atom, and n is an integer of 1 to 3.

9 Claims, 2 Drawing Sheets

SULFONIUM BORATE COMPLEX

TECHNICAL FIELD

The present invention relates to a novel sulfonium borate complex which is useful as a thermal cationic polymerization initiator.

BACKGROUND ART

Conventionally, photocationic polymerizable adhesives containing an epoxy resin as a main component have been used as one kind of adhesive used when mounting an electronic part, such as an IC chip, on a circuit board. A photocationic polymerization initiator, in which protons are generated by light to cause cationic polymerization to start, is blended into such a photocationic polymerizable adhesive. Sulfonium antimonate complexes are known as such a photocationic polymerization initiator.

However, sulfonium antimonate complexes have as a counter anion $SbF_6^-$, in which fluorine atoms are bonded to the metal antimony, so that fluorine ions are produced in large amounts during cationic polymerization. This causes problems with corrosion of the metal wiring and connection pads. Thus, the use of a sulfonium borate complex as a cationic polymerization initiator which uses instead of $SbF_6^-$ a tetrakis (pentafluorophenyl)borate anion [$(C_6F_5)_4B^-$], in which the fluorine atoms are bonded to a carbon atom, has been proposed (Patent Document 1). In fact, the complex [p-hydroxyphenyl-benzyl-methyl sulfonium tetrakis(pentafluorophenyl)borate] of the following formula (1c) is commercially available.

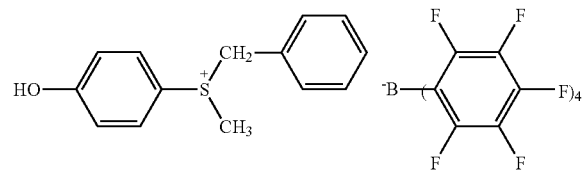

(1c)

However, when mounting an electronic part on a circuit board, in many cases the joining portion cannot be irradiated with light. Thus, attempts are being made to convert the specific sulfonium borate complex disclosed in the examples of Patent Document 1 into a thermal cationic polymerization initiator for a thermal cationic polymerizable adhesive. In such a case, not only is it required to reduce the amount of fluorine ions produced during cationic polymerization and improve the electrochemical corrosion resistance of the thermal cationic polymerizable adhesive, but in order to improve productivity, the low-temperature, rapid curing properties of the thermal cationic polymerizable adhesive also need to be improved.

[Patent Document 1] Japanese Patent Application Laid-open No. Hei 9-176112

DISCLOSURE OF THE INVENTION

Problems to be Solved by the Invention

However, when the complex of the formula (1c) is used as a thermal cationic polymerization initiator, although the amount of fluorine ions produced during thermal cationic polymerization can be reduced to a certain extent, the low-temperature, rapid curing properties cannot be said to be sufficient.

The present invention solves the above-described problems in the conventional art. It is an object of the present invention to provide a novel sulfonium borate complex which can reduce the amount of fluorine ions produced during thermal cationic polymerization, and can realize low-temperature, rapid curing properties in a thermal cationic polymerizable adhesive.

Means for Solving the Problems

The present inventor discovered that the above objectives could be achieved by introducing a novel combination of three specific substituents onto the sulfonium residue of a sulfonium borate complex, thereby completing the present invention.

Specifically, the present invention is a sulfonium borate complex represented by the formula (1).

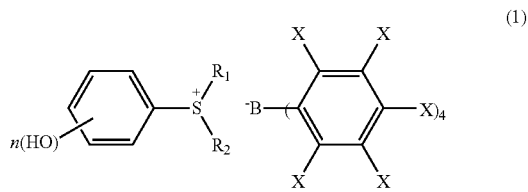

(1)

In the formula (1), $R_1$ is an aralkyl group and $R_2$ is a lower alkyl group. However, when $R_2$ is a methyl group, $R_1$ is not a benzyl group. X is a halogen atom, and n is an integer of 1 to 3.

Furthermore, the present invention is a method for producing the sulfonium borate complex of the formula (1), wherein the sulfonium borate complex of the formula (1) is obtained by reacting a sodium borate salt of the formula (3) with a sulfonium antimonate complex of the formula (2).

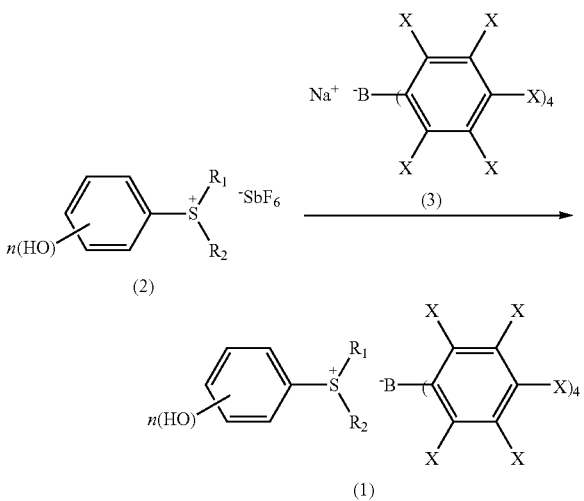

In the formula (1), (2), or (3), $R_1$ is an aralkyl group and $R_2$ is a lower alkyl group. However, when $R_2$ is a methyl group, $R_1$ is not a benzyl group. X is a halogen atom, and n is an integer of 1 to 3.

ADVANTAGES OF THE INVENTION

The three substituents of the novel sulfonium borate complex of the formula (1) according to the present invention are a novel combination. Thus, during thermal cationic polymerization of a thermal cationic polymerizable adhesive containing this complex as a thermal cationic polymerization initiator, the amount of fluorine ions produced can be reduced, and in addition low-temperature, rapid curing properties can be realized.

BEST MODE FOR CARRYING OUT THE INVENTION

Figure 1:
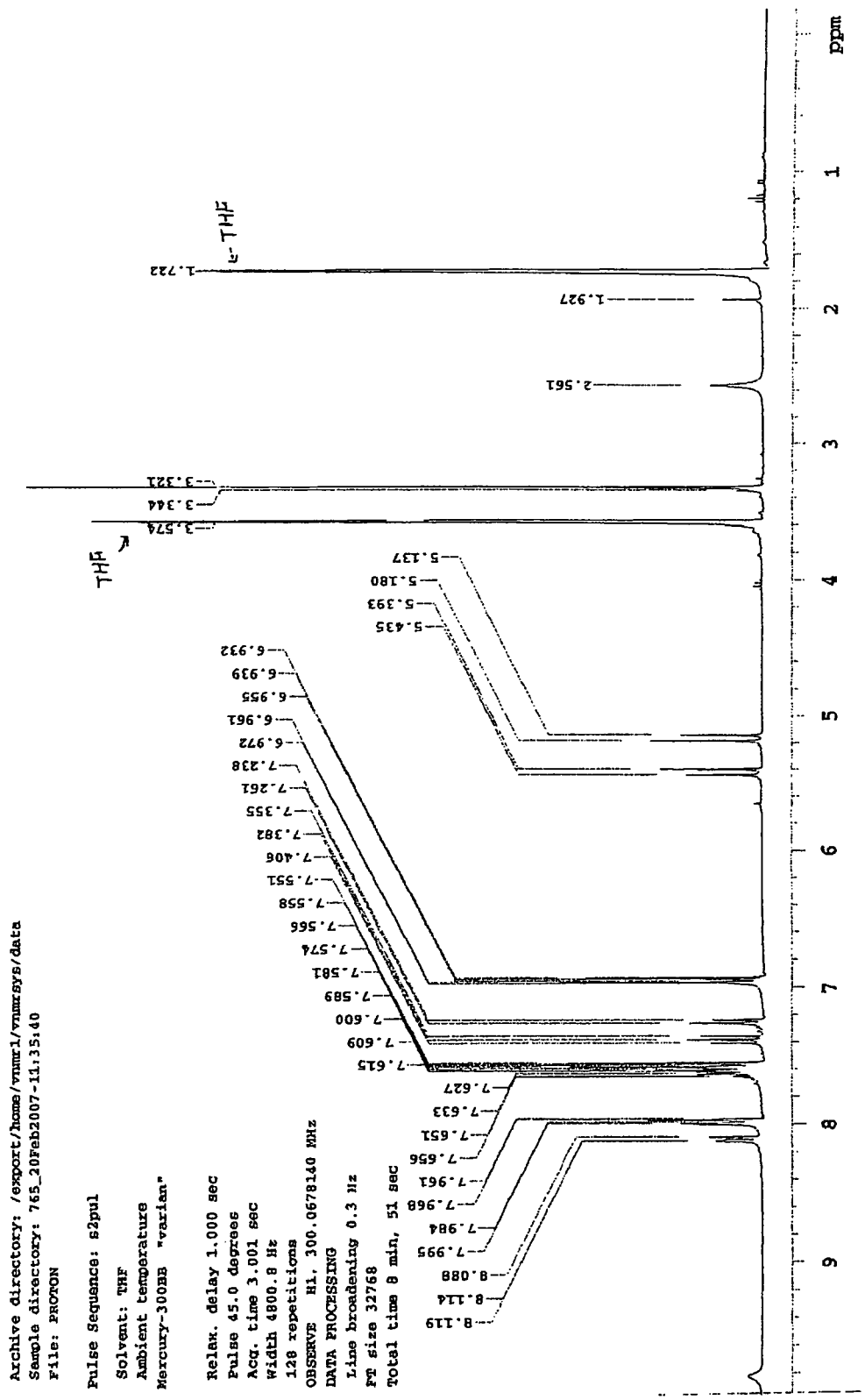
FIG. 1 is a $^1$H-NMR chart of the sulfonium borate complex of Example 1.

The novel compound according to the present invention is a sulfonium borate complex represented by the formula (1).

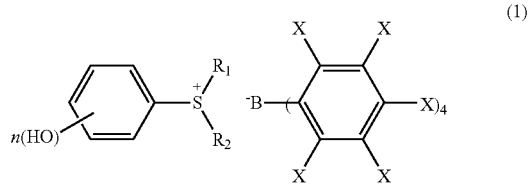

In the formula (1), examples of the $R_1$ aralkyl group include a benzyl group, an o-methylbenzyl group, a (1-naphthyl)methyl group, a pyridylmethyl group, an anthracenylmethyl group and the like. Among these, a (1-naphthyl)methyl group is preferred from the standpoint of good, rapid curing properties and ease of availability.

Examples of the $R_2$ lower alkyl group include a methyl group, an ethyl group, a propyl group, a butyl group and the like. Among these, a methyl group is preferred from the standpoint of good, rapid curing properties and ease of availability. However, when the $R_2$ lower alkyl group is a methyl group, the $R_1$ aralkyl group is not a benzyl group.

The number of hydroxyl groups of the phenyl group bonded to the sulfonium residue, i.e., "n" is an integer of 1 to 3. Examples of such a phenyl group include, for when n is 1, a 4-hydroxyphenyl group, a 2-hydroxyphenyl group, a 3-hydroxyphenyl group or the like; for when n is 2, a 2,4-dihydroxyphenyl group, a 2,6-dihydroxyphenyl group, a 3,5-dihydroxyphenyl group, a 2,3-dihydroxyphenyl group and the like; and for when n is 3, a 2,4,6-trihydroxyphenyl group, a 2,4,5-trihydroxyphenyl group, a 2,3,4-trihydroxyphenyl group and the like. Among them, from the standpoint of good, rapid curability and ease of availability, a 4-hydroxyphenyl group is preferred.

Examples of the halogen atom of X include a fluorine atom, a chlorine atom, a bromine atom, or an iodine atom. Among them, from the standpoint of improving reactivity, a fluorine atom having high electron withdrawing properties is preferred.

The novel sulfonium borate complex of the formula (1) according to the present invention can be produced according to the following reaction formula. In the formula (1), (2), or (3), $R_1$ is an aralkyl group and $R_2$ is a lower alkyl group. However, when $R_2$ is a methyl group, $R_1$ is not a benzyl group. X is a halogen atom, and n is an integer of 1 to 3.

<Reaction Formula>

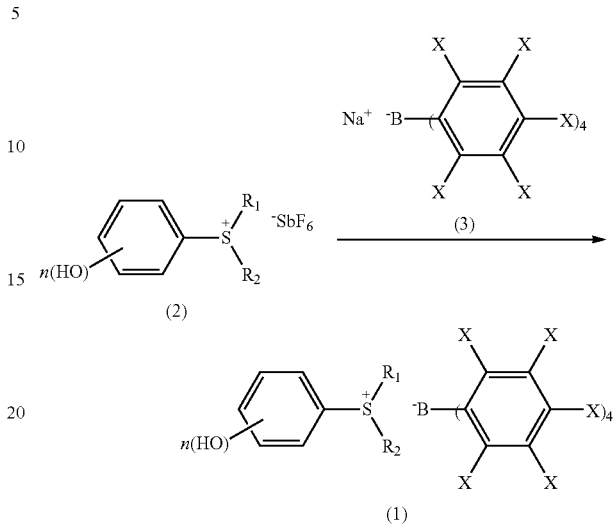

Specifically, the sulfonium borate complex of the formula (1) can be obtained by reacting the sodium borate salt of the formula (3) with the sulfonium antimonate complex of the formula (2), by dissolving the sulfonium antimonate complex (refer to Japanese Patent Application Laid-Open No. Hei 10-245378 for the synthesis method) of the formula (2) in an organic solvent such as ethyl acetate, mixing into the resultant solution an aqueous solution of a sodium borate salt of the formula (3) (refer to Japanese Patent Application Laid-Open No. Hei 10-310587 for the synthesis method) in an equimolar amount, and stirring the resultant bilayer system mixture for 1 to 3 hours at a temperature of 20 to 80° C. Isolation of the sulfonium borate complex of the formula (1) can be carried out by separating the organic solvent layer, drying the layer, and then removing the organic solvent by evaporation under reduced pressure to thereby obtain the target product as an evaporated residue.

The novel sulfonium borate complex of the formula (1) according to the present invention can be used as a thermal cationic polymerization initiator for general epoxy resins. In this case, an epoxy resin composition (in a paste or film form) containing 100 parts by mass of epoxy resin and 0.1 to 10 parts by mass of the novel sulfonium borate complex of the formula (1) as a thermal cationic polymerization initiator, can give cured matter which has excellent electrochemical corrosion resistance and which is cured rapidly at a low temperature by heating at 50 to 150° C.

EXAMPLES

Examples 1 and 2, Comparative Examples 1 to 4

The sulfonium antimonate complexes of the formulae (1d), (1e), and (1f) (refer to Japanese Patent Application Laid-Open No. Hei 10-245378 for the synthesis method) were dissolved in ethyl acetate to prepare respective 10 mass % solutions of such complex in ethyl acetate. Separately, an aqueous solution of 10 masse of the sodium borate salt of the formula (3) (refer to Japanese Patent Application Laid-Open No. Hei 10-310587 for the synthesis method) was prepared.

Next, the aqueous solution of 10 mass % of the sodium borate salt of the formula (3) was mixed at room temperature in an equimolar amount into the 10 mass % solutions of the complexes in ethyl acetate, and the resultant mixtures were stirred as is for 30 minutes. Then, the ethyl acetate layer was separated from the reaction mixtures. The layers were dried, and the ethyl acetate was removed under reduced pressure, whereby the sulfonium borate complex of the formula (1a) of Example 1, the sulfonium borate complex of the formula (1b) of Example 2, and the sulfonium borate complex of (1c) of Comparative Example 1 were obtained as evaporated residues.

-continued

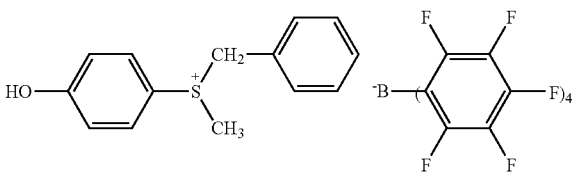
(1c)

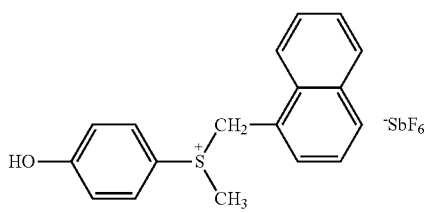
(1d)

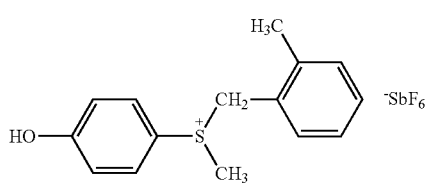
(1e)

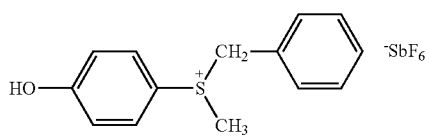
(1f)

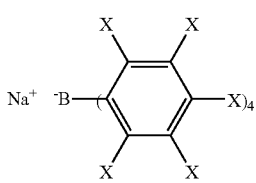
(3)

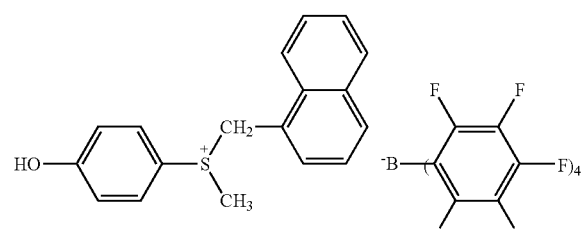
(1a)

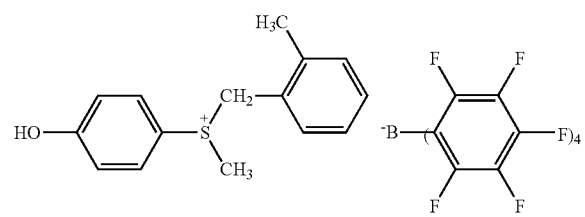
(1b)

The novel compound sulfonium borate complexes of the formula (1a) and (1b) were subjected to mass spectroscopy (measuring instrument: ACQUITY UPLC System, Waters), elemental analysis (measuring instrument: PHOENIX, EDAX), IR analysis (measuring instrument: 7000e FT-IR, Varian), and $^1$H-NMR analysis (measuring instrument: MERCURY PLUS, Varian). It was confirmed from the obtained results that the complexes were the target compounds.

Analysis Results of the Sulfonium Borate Complex of Formula (1a)
[4-hydroxyphenyl-methyl-1-naphthylmethyl sulfonium tetrakis(pentafluorophenyl)borate]

<MS Analysis Results>
M$^+$=281 (sulfonium residue)
M$^+$=679 (borate residue)

<Elemental Analysis Results>
Actual Measured Values: C, 52.51; H, 1.89
Theoretical Values: C, 52.52; H, 1.78

<IR Analysis Results (cm$^{-1}$)>
662 (C—S), 776, 980, 1088, 1276 (Ar—F), 1300, 1374, 1464, 1514, 1583, 1643, 2881 (C—H), 2981 (C—H), 3107 (O—H)

<$^1$H-NMR Analysis Results (δ value), Refer to FIG. 1 (Using THF)>
2.6 (1H, (d)), 3.3 (3H, (a)), 5.3 (2H, (e)), 6.9 (2H, (c)), 7.6 (2H, (b)), 7.2-8.1 (7H, (f), (g), (h), (i), (j), (k) (l))

(Proton Assignment)

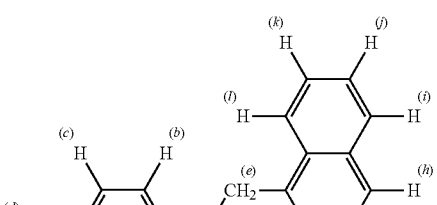

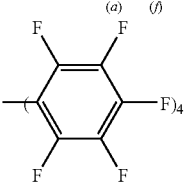

Analysis Results of the Sulfonium Borate Complex
of Formula (1b)
[4-hydroxyphenyl-methyl-(2-methylbenzyl)
sulfonium tetrakis(pentafluorophenyl)borate]

Figure 2:
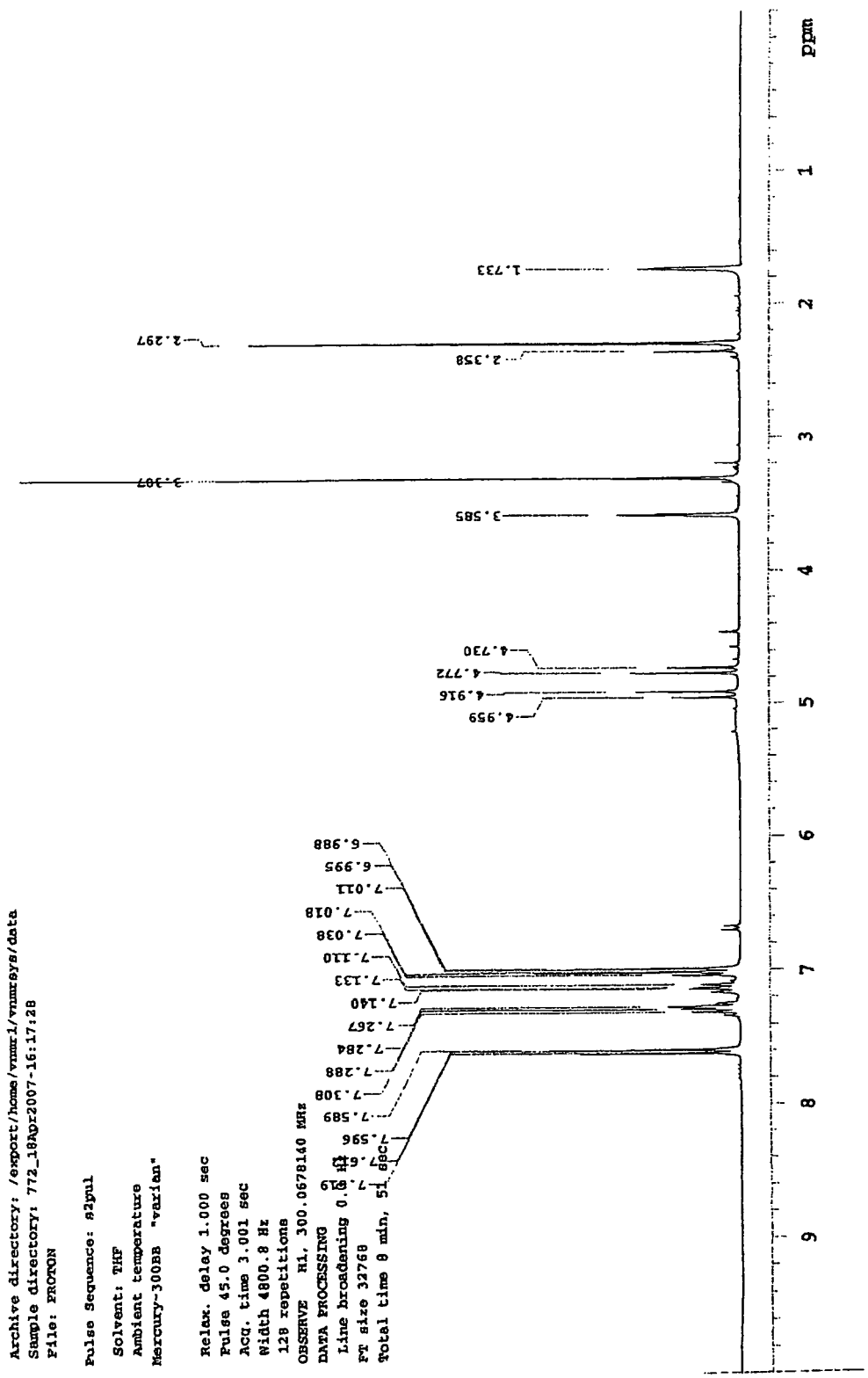
FIG. 2 is a $^1$H-NMR chart of the sulfonium borate complex of Example 2.

<MS Analysis Results>
  $M^+$=245 (sulfonium residue)
  $M^+$=679 (borate residue)
<Elemental Analysis Results>
  Actual Measured Values: C, 50.39; H, 1.77
  Theoretical Values: C, 50.60; H, 1.80
<IR Analysis Results ($cm^{-1}$)>
  662 (C—S), 773, 980, 1088, 1276 (Ar—F), 1463, 1514, 1583, 1644, 2882 (C—H), 2983 (C—H), 3109 (O—H)
<$^1$H-NMR Analysis Results (δ value), Refer to FIG. 2 (Using THF)>
  2.3 (3H, (j)), 2.4 (1H, (d)), 3.3 (3H, (a)), 4.8 (2H, (e)), 7.0 (2H, (c)), 7.6 (2H, (b)), 7.0-7.4 (4H, (f), (g), (h), (i))

(Proton Assignment)

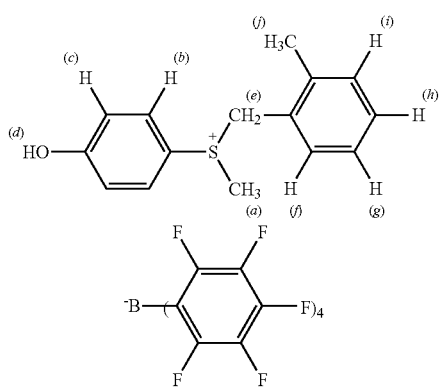

Property Evaluation

Each of the sulfonium borate complexes of Examples 1 and 2 and Comparative Example 1, and the sulfonium antimonate complexes of the formulae (1d), (1e), and (1f) as Comparative Examples 2 to 4, had their fluorine ion concentration measured as described below under the temperature conditions of during the thermal cationic polymerization. Furthermore, a thermal cationic polymerizable composition was prepared. This composition was subjected to differential scanning calorimetry (DSC analysis) at a rate of temperature increase of 10° C./min.

Measurement of Fluorine Ion Concentration 0.2 g of a complex was charged into 10 mL of pure water, and the resultant mixture was heated for 10 hours at 100° C. Then, the amount of fluorine ions in the supernatant was measured by ion chromatography analysis (Dionex Corporation). The obtained results are shown in Table 1. In practice, less than 10 ppm is desirable.

DSC Analysis

Thermal cationic polymerizable compositions were produced by mixing 1 part by mass of complex for Example 1 or 2, 3 parts by mass of complex for Comparative Example 1, or 5 parts by mass of complex for Comparative Examples 2 to 4, into 100 parts by mass of liquid epoxy resin (Epicoat 828, Japan Epoxy Resins Co., Ltd.). These compositions were subjected to differential thermal analysis (exothermic onset temperature, peak temperature, and calorific value) using a thermal analysis apparatus (DSC 5100, Seiko Instruments Inc.). The obtained results are shown in Table 1.

The exothermic onset temperature is the temperature at which protons are generated from the complex and cationic polymerization starts. Although the lower the exothermic onset temperature is, the better the low-temperature curing properties become, because storage stability tends to deteriorate, in practice 80 to 110° C. is preferable. Furthermore, if the exothermic peak temperature is too low, storage stability deteriorates, while if the exothermic peak temperature is too high, curing defects tend to occur. Thus, in practice 100 to 140° C. is preferable. The calorific value corresponds to the heat of reaction. Since curing defects tend to occur if the calorific value is too small, in practice this value is preferably 200 J/g or more.

TABLE 1

| (Complex) | F Ion Concentration (ppm) | Exothermic Onset Temperature (° C.) | Exothermic Peak Temperature (° C.) | Calorific Value (J/g) |
|---|---|---|---|---|
| Example 1 (1a) | 2.1 | 85 | 114 | 250 |
| Example 2 (1b) | 2.3 | 105 | 134 | 320 |
| Comparative Example 1 (1c) | 2.3 | 115 | 147 | 270 |
| Comparative Example 2 (1d) | 160,000 | 83 | 118 | 290 |
| Comparative Example 3 (1e) | 170,000 | 106 | 135 | 300 |
| Comparative Example 4 (1f) | 172,000 | 116 | 146 | 280 |

In the case of the novel sulfonium borate complexes of the formula (1) of Examples 1 and 2, the fluorine ion concentration was less than 10 ppm, the exothermic onset temperature by DSC analysis was in the range of from 80 to 110° C., the exothermic peak temperature was in the range of from 100 to 140° C., and the calorific value was 200 J/g or more. Thus, these complexes were in practice satisfactory.

On the other hand, in the case of Comparative Example 1, there were problems with the evaluation results of the exothermic onset temperature and exothermic peak temperature evaluation criteria. Furthermore, in the case of Comparative Examples 2 and 3, there were problems with the evaluation results of the fluorine ion concentration evaluation criteria, and in the case of Comparative Example 4, there were problems with the evaluation results of the fluorine ion concentration, exothermic onset temperature, and exothermic peak temperature evaluation criteria.

INDUSTRIAL APPLICABILITY

The novel sulfonium borate complex according to the present invention is useful as a thermal cationic polymerization initiator, since it can reduce the amount of fluorine ions produced during thermal cationic polymerization, and can realize low-temperature, rapid curing properties in a thermal cationic polymerizable adhesive.

The invention claimed is:

1. A sulfonium borate complex represented by the formula (1);

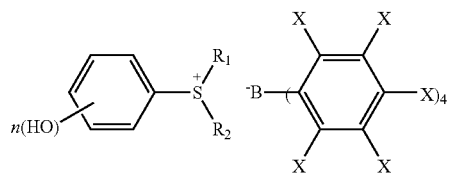

in the formula (1), $R_1$ is an o-methylbenzyl group or a (1-naphthyl)methyl group and $R_2$ is a methyl group; X is a halogen atom, and n is an integer of 1 to 3.

2. The sulfonium borate complex according to claim 1, wherein n is 1, and a phenyl group connecting with an OH group is a 4-hydroxyphenyl group.

3. The sulfonium borate complex according to claim 1, wherein X is a fluorine atom.

4. A method for producing the sulfonium borate complex of the formula (1) according to claim 1, the method comprising reacting a sodium borate salt of the formula (3) with a sulfonium antimonate complex of the formula (2) to obtain the sulfonium borate complex of the formula (1);

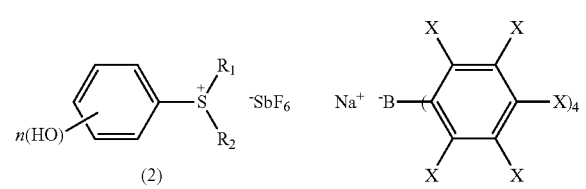

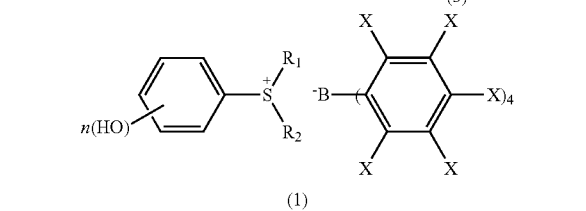

wherein, in the formula (1), (2), or (3), $R_1$ is an o-methylbenzyl group or a (1-naphthyl)methyl group and $R_2$ is a methyl group; X is a halogen atom, and n is an integer of 1 to 3.

5. The sulfonium borate complex according to claim 2, wherein X is a fluorine atom.

6. A sulfonium borate complex represented by the formula (1a)

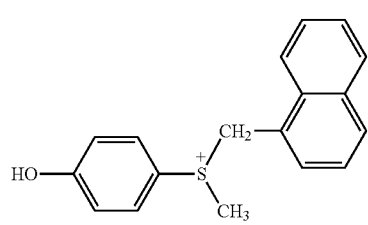

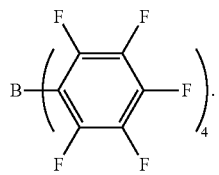

7. A sulfoniun borate complex represented by the formula (1b)

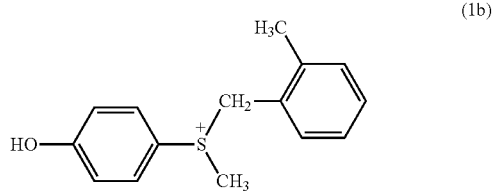

8. A method for producing the sulfonium borate complex of the formula (1a) according to claim 6, the method comprising reacting a sodium borate salt of the formula (3) with a sulfonium antimonate complex of the formula (2) to obtain the sulfonium borate complex of the formula (1a)

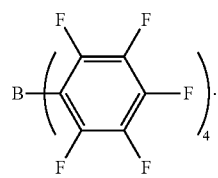

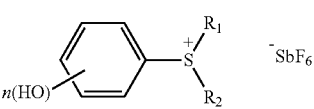

wherein, in the formula (2) or (3), $R_1$ is a (1-napthylmethyl) group and $R_2$ is a methyl group; X is a fluorine atom, and n is 1.

9. A method for producing the sulfonium borate complex of the formula (1b) according to claim 7, the method comprising reacting a sodium borate salt of the formula (3) with a sulfonium antimonate complex of the formula (2) to obtain the sulfonium borate complex of the formula (1b)
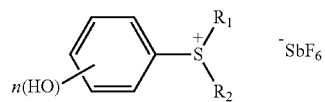
(2)
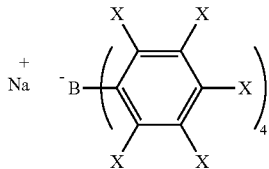
(3)
wherein, in the formula (2) or (3), $R_1$ is an o-methylbenzyl group and $R_2$ is a methyl group; X is a fluorine atom and n is 1.
* * * * *